United States Patent
Carey et al.

(10) Patent No.: US 9,750,290 B2
(45) Date of Patent: Sep. 5, 2017

(54) PASSIVE MECHANICAL EXOSKELETON TO REDUCE HAND FATIGUE

(71) Applicant: THE REGENTS OF THE UNIVERSITY OF CALIFORNIA, Oakland, CA (US)

(72) Inventors: Alan Carey, Davis, CA (US); Stephen Robinson, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/267,039

(22) Filed: Sep. 15, 2016

(65) Prior Publication Data

US 2017/0071272 A1    Mar. 16, 2017

Related U.S. Application Data

(60) Provisional application No. 62/219,477, filed on Sep. 16, 2015.

(51) Int. Cl.
*A41D 19/015* (2006.01)
*A61F 5/01* (2006.01)

(52) U.S. Cl.
CPC . *A41D 19/01582* (2013.01); *A41D 19/01547* (2013.01); *A61F 5/013* (2013.01)

(58) Field of Classification Search
CPC .................... A41D 19/01582; A41D 19/01547
USPC ........... 294/25, 111; 2/159, 160, 161.4, 162; 601/23, 40; 602/22; 482/47, 124; 414/5; 700/250

See application file for complete search history.

(56) References Cited

U.S. PATENT DOCUMENTS

| | | | | |
|---|---|---|---|---|
| 4,084,267 A | * | 4/1978 | Zadina | A61F 2/54 602/22 |
| 5,184,319 A | * | 2/1993 | Kramer | G06F 3/011 345/156 |
| 5,472,410 A | * | 12/1995 | Hamersly | A61F 5/0125 601/33 |
| 5,538,488 A | * | 7/1996 | Villepigue | A63B 21/0004 482/44 |
| 5,643,186 A | * | 7/1997 | Chinchalkar | A61F 5/0118 601/40 |

(Continued)

OTHER PUBLICATIONS

Sorenson, E.A. et al., "Design and Preliminary Test Results from a Second Generation Power-Assisted Space Suit Glove Joint", SAE Technical Paper Series 98164, 28th International Conference of Environmental Systems, Denvers, MA, Jul. 13-16, 1988, pp. 1-6 (8 pages including cover pages).

(Continued)

*Primary Examiner* — Paul T Chin
(74) *Attorney, Agent, or Firm* — John P. O'Banion

(57) ABSTRACT

A passive mechanical system comprising an unpowered exoskeleton to maintain static grip around an object via a tendon drive and ratchet mechanism. The ratchet mechanism combines a passive cable retract and ratchet system with one or more cables acting as artificial tendons. When a user wishes to keep their hand in a specific position around an object, the ratchet system is engaged. A cable retract mechanisim keeps the artifical tendon taught at all times. The combination of these systems allows for the user to keep grip on objects without the need to input force over time thereby reducing fatigue.

23 Claims, 9 Drawing Sheets

(56) References Cited

U.S. PATENT DOCUMENTS

| | | | | |
|---|---|---|---|---|
| 6,059,506 A * | 5/2000 | Kramer | ................ | G06F 3/011 |
| | | | | 414/5 |
| 6,312,398 B1 | 11/2001 | Cencer | | |
| 7,410,338 B2 * | 8/2008 | Schiele | ............ | A61H 1/0274 |
| | | | | 414/4 |
| 8,029,414 B2 * | 10/2011 | Ingvast | ............ | A61H 1/0288 |
| | | | | 482/4 |
| 8,255,079 B2 | 8/2012 | Linn et al. | | |
| 2010/0175163 A1 * | 7/2010 | Litke | ..................... | A41F 1/06 |
| | | | | 2/161.4 |
| 2011/0185473 A1 * | 8/2011 | Voravan | ............ | A41D 19/00 |
| | | | | 2/161.2 |
| 2013/0219585 A1 * | 8/2013 | Bergelin | ............ | B25J 9/0006 |
| | | | | 2/160 |
| 2013/0219586 A1 | 8/2013 | Ihrke et al. | | |
| 2013/0226350 A1 | 8/2013 | Bergelin et al. | | |
| 2016/0058130 A1 * | 3/2016 | Boney | ................ | A43C 1/06 |
| | | | | 24/712.6 |

OTHER PUBLICATIONS

Shields, Bobby L. et al., "An Anthropomorphic Hand Exoskeleton to Prevent Astronaut Hand Fatigue During Extravehicular Activities", IEEE Transactions on Systems, Man, and Cybernetics—Part A: Systems and Humans, vol. 27, No. 5, Sep. 1997, pp. 668-673.

* cited by examiner

PASSIVE MECHANICAL EXOSKELETON TO REDUCE HAND FATIGUE

CROSS-REFERENCE TO RELATED APPLICATIONS

This application claims priority to, and the benefit of, U.S. provisional patent application Ser. No. 62/219,477 filed on Sep. 16, 2015, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

This description pertains generally to a mechanical exoskeleton, and more particularly to a passive mechanical exoskeleton for extravehicular activity (EVA).

2. Background Discussion

Many systems have attempted to improve grip strength and reduce fatigue in the hands of operators. However, all of these systems have introduced bulk to the hand and palm making the system difficult to operate, or introduce the need for external power sources and computer control.

Astronaut hand fatigue during Extravehicular Activity (EVA) and EVA training is a critical risk in human space exploration. Improved glove designs over the past forty years have reduced hand fatigue, but limitations of the technology prevent major improvements to reduce hand fatigue. Therefore, a mechanism to assist astronauts by reducing hand fatigue was explored. Existing exoskeletons to assist astronauts generally involve electrically powered actuators and control systems to enhance grip strength. However, astronauts already possess the strength required to actuate the glove; what is needed is a method to reduce fatigue without introducing electromechanical complexity.

BRIEF SUMMARY

An aspect of the present technology is a passive mechanical system comprising an unpowered exoskeleton to maintain static grip around an object. The technology described herein seeks to reduce the fatigue experienced by a user while gripping an object for a period of time, and in particular astronauts in their hands while wearing pressurized gloves. This is achieved via a tendon drive and ratchet mechanism.

In one embodiment, a ratchet combines a passive cable retract and ratchet system with one or more cables acting as artificial tendons. When a user wishes to keep their hand in a specific position around an object, the ratchet system is engaged. A cable retract mechanism keeps the artifical tendon taught at all times. The combination of these systems allows for the user to keep grip on objects without the need to input force over time thereby reducing fatigue.

In one embodiment, a cable is attached to the fingertip, and routed through one or more "saddles" or "guides" located on one or more of the digits on each finger. Once at the palm, the array of saddles or guides collects the four cables (one for each finger) and guide the cables into one or more sheaths that extend proximally down the palm. From the palm, the one or more sheaths and cables rotate around the wrist to the distal side of the hand (aka back of the hand). The one or more sheaths feed into the ratchet and retract mechanism.

In one embodiment, the ratchet and retract mechanism comprises a spool, ratchet gear with pawl, and a spring all contained in a housing. The cables are directly connected to the spool. One end of the spool contains a ratchet gear which engages with a pawl. When in the first position, the pawl is not engaged with the ratchet and free movement is allowed. When the pawl is in the second position, the teeth on the pawl engage with the ratchet, restricting the spindle to one way movement. The spring is connected between the housing and spool, and provides a torque to the spool which always tensions the cables.

In one embodiment, the spring is pre-tensioned when the hand is in the open position. As the user closes his/her hand, the spring and spool take up the slack from the cable. If the ratchet is in the second position (engaged), the ratchet will "click'" but allow the spool to spin. When the user stops closing his/her hand, the ratchet, if in second position, engages and restricts cord from being pulled out of the mechanism; therefore, the wearer's hand is locked in position. To disengage, the user flips a toggle coupled to the pawl to the first position, and opens his/her hand.

The systems and methods of the present disclosure provide reducing fatigue, but without introducing the complexity of electromechanical systems. The lack of complexity introduces ease-of-use and improved saftey during use.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

In general terms, the technology described herein is a mechanical system that combines a tendon driven system with a passive mechanical ratchet and glove. This combination provides a novel system with applications not only to aerospace, but also other applications such as sporting equipment and safety equipment.

I. System Configuration

Figure 1:
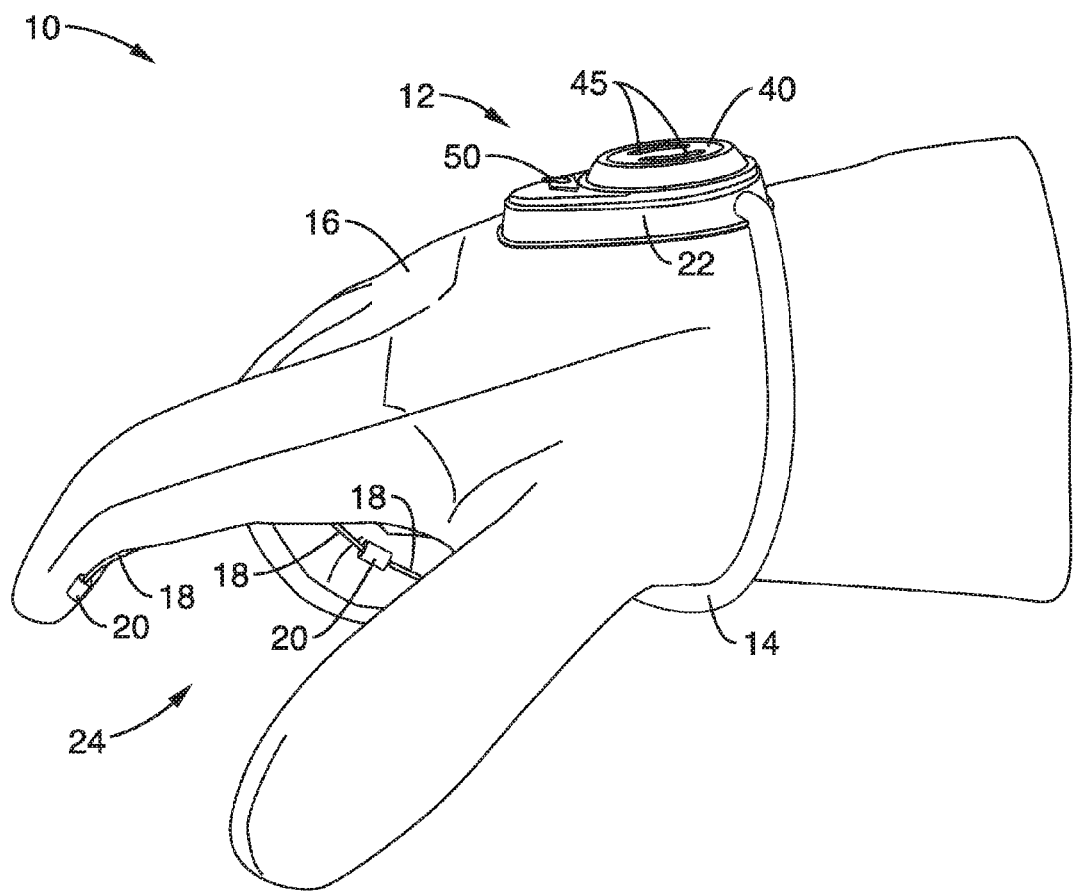
FIG. 1 shows a perspective radial-dorsal view of the passive mechanical exoskeleton attached to a glove in accordance with the present disclosure.
Figure 2:
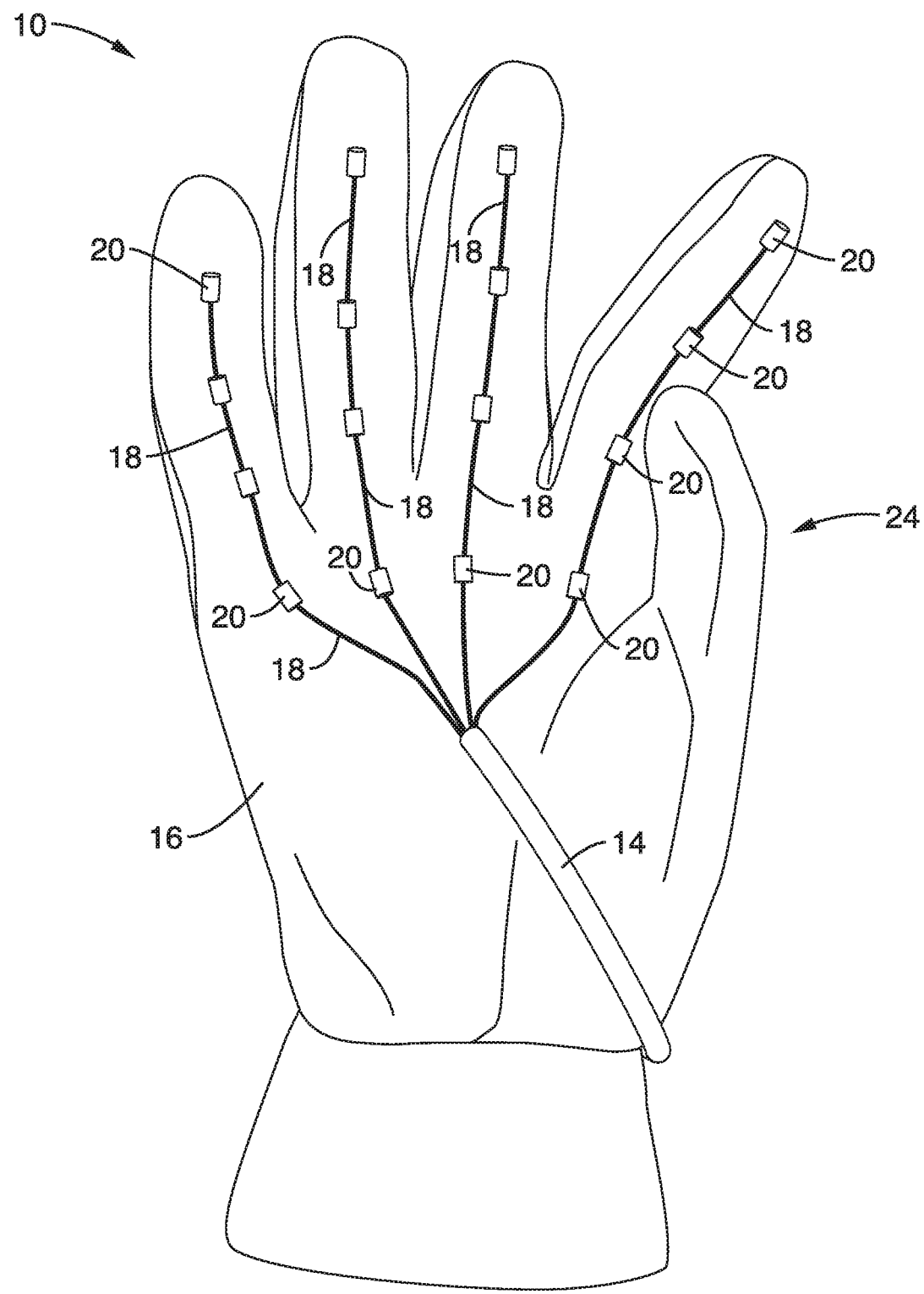
FIG. 2 shows a palmar view detailing the tendon drive of the passive mechanical exoskeleton of FIG. 1.

FIG. 1 shows a perspective radial-dorsal view of the passive mechanical exoskeleton system 10 attached to a glove 16 in accordance with the present disclosure. While the individual components of system 10 are shown attached or fastened to glove 16, it is appreciated that system 10 may comprise a glove that is integrated or integral with the tendon drive mechanism 24 and ratchet mechanism 12 built into the glove. The glove 16 shown in FIG. 1 and FIG. 2 is also illustrated in a generic form, as it is appreciated that the system 10 may be configured for gloves of varying application (e.g., a pressurized glove for EVA, work glove for extended grip with tools, safety glove to act as a tether for fall protection, etc.). It is also appreciated that system 10 may be configured as a stand-alone device configured to releasably attach to an existing glove, e.g., by use of straps or other fastening means, or as a self-contained sleeve that fits under over or under an existing glove.

To allow attachment of the ratchet mechanism 12 to the glove 16, a housing adapter 22 may be provided. The housing adapter 22 is configured to accept both the ratchet mechanism 12 and cable sleeve 14. In one embodiment, the housing adapter 22 is sewn into the glove 16. In a releasable configuration of system 10, the housing adapter may be integrated with or otherwise attached to nylon webbing (not shown) for attaching to the user's palm.

By way of example, and not of limitation, the system 10 as illustrated in FIG. 1 functions as follows:

1) The subject applies glove 16 with attached or integrated passive mechanical exoskeleton system 10.

2) The subject grasps an object with his/her hand (i.e., the fingers are placed in flexion when fingers close toward the palm).

3) When the desired orientation of the subject's fingers is reached, the subject actuates toggle 50 to engage the ratchet assembly 12. This acts to restrain motion (primarily in the extension direction (opening away from the palm)) of one or more of the user's fingers via the tendon drive mechanism 24, which comprises one or more cables or cords 18 attached or coupled to the fingers via one or more standoffs or guides 20. The cords 18 of the tendon drive mechanism 24 are coupled to the ratchet mechanism 12 by use of a sleeve 14 that runs palmar to dorsal around the side of the hand (shown along the radial side of the hand in FIG. 1, although a ulnar route may also be configured). It is also appreciated that the toggle 50 may be actuated for one-way engagement prior to gripping or flexion. In this manner, the ratchet mechanism 12 allows for the retraction of the tendon cable 18, but restricts the tendon cable 18 from being pulled out.

4) Additional torque in the system 10 can be provided via the other hand by rotating the housing core 40. In one embodiment, a spanner wrench (not shown) may be applied to grooves 45 of housing core 40 to provide additional torque. It is appreciated that other configurations may be implemented for inducing additional torque into the system 10 without use of a tool, or the user's second hand.

5) When the subject wishes to let go, the toggle 50 is rotated (in opposite direction) to disengage the ratchet mechanism 12.

6) The subject opens his/her hand (i.e., the fingers are placed in extension opening away from the palm) to release the grasped object.

FIG. 2 shows a palmar view detailing the tendon drive mechanism 24 of the passive mechanical exoskeleton 10. In one embodiment, one or more tendon cables or cords 18 are attached to a distal location of one or more fingers (i.e., at each fingertip), and routed through a plurality of guides or standoffs 20 located on one or more locations of the digits on each finger. Once at the palm, the array of guides 20 collects the plurality of cables (e.g., four cables would be used for four-finger configuration at each finger) and guides the tendon cables 18 into one or more sheaths 14 that extend proximally down the palm. From the palm, the one or more sheaths 14 and tendon cables 18 rotate around the wrist to the dorsal side of the hand (i.e., the back of the hand). The one or more sheaths then couple into the ratchet mechanism 12.

In one embodiment, the tendon cables 18 and sheath 14 are disposed in the form of a Bowden cable, which transfers force along a tendon cable 18 relative to a sheath 14 in the for of a flexible guide 14. In one embodiment, the sheath 14 comprises a flexible vacuum rated tube. A larger inner diameter (e.g., approximately 6 mm) may be used to allow for multiple tendons/cables to pass into the housing, as shown in FIG. 2. Alternatively, multiple sleeves (not shown) may be used for each tendon cable 18, or the plurality of cables may be fused at a juncture of a single tendon cable 18 that is fed to the ratchet mechanism 12.

The tendon cord or cable 18 is the primary load carrier throughout the system 10. As can be seen by the trend in the plot of cord tension vs. grip force of FIG. 13, for the measured data, grip force will have a lower magnitude than the cord tension. Therefore, the tendon cable 18 should be of high strength, while remaining being flexible to conform to closed glove geometry, and be low friction when interacting with the guides 20 and sheath 14. While steel cable is of high strength, it is not flexible enough. Fishing line monofilament is flexible, but not strong enough. An adequate compromise was found with woven 1 mm diameter ultrahigh-molecular-weight polyethylene (e.g., Spectra or Dyneema) coated with a polyurethane resin, having a strength of 1472 N.

In one embodiment, the guides 20 comprise small tubes or sleeves that are made from nylon (vacuum) tubing having an inner diameter of 2.8 mm, 0.6 mm wall thickness, and 7 mm length. Such tubing resists crushing and has thin walls (when compared to tygon tubing).

In a further embodiment, the guides 20 are sewn or integrated into glove 16. It is also appreciated that guides 20 may be sewn into pieces of nylon webbing to allow for releasable attachment to the glove 16 to allow for adjustment and experimentation. When the tendon cables 18 are pulled in flexion, the distance between the tendon guides 20 reduces. As the center of rotation is not in the same plane as the tendon guides 20, the finger must rotate closed. FIG. 2 shows implementation of four tendon cables 18 and corresponding set of guides 20. However, it is appreciated that any number or combination of tendon cables 18 and guides 20 may be placed on various fingers and/or the thumb.

Due to space suit design restrictions, the ratchet mechanism 12 was positioned at approximately the back of the hand. Ideally, the ratchet mechanism 12 is best located on the forearm. Thus, for non-EVA applications, ratchet mechanism 12 location may vary.

Figure 3:
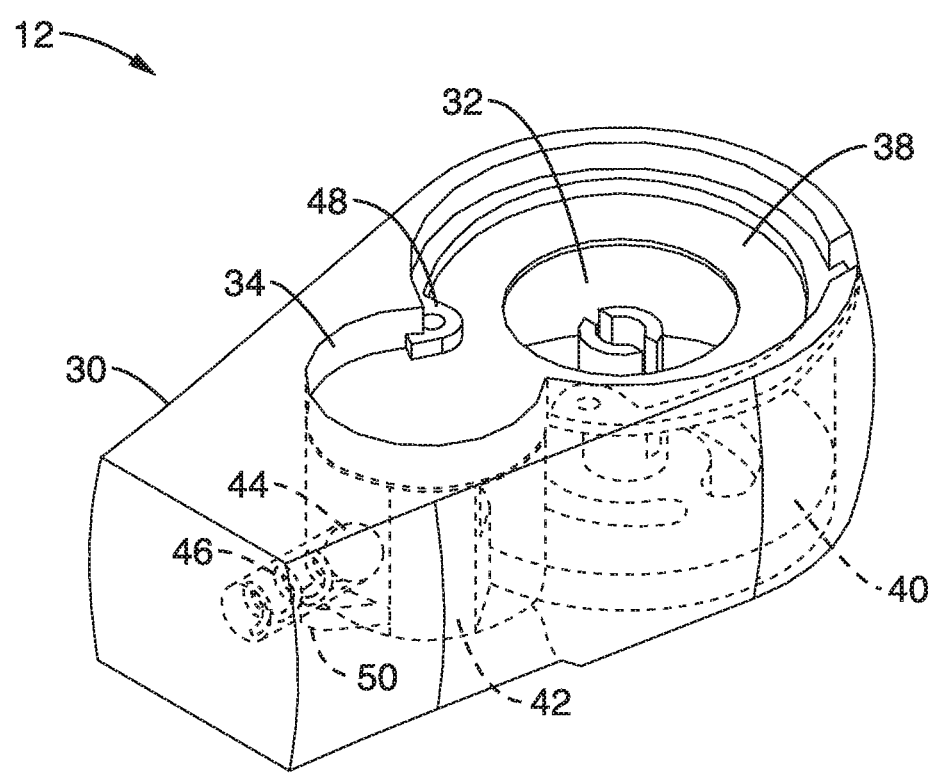
FIG. 3 shows a perspective view of the ratchet mechanism of the passive mechanical exoskeleton of FIG. 1 without spool subassembly.
Figure 4:
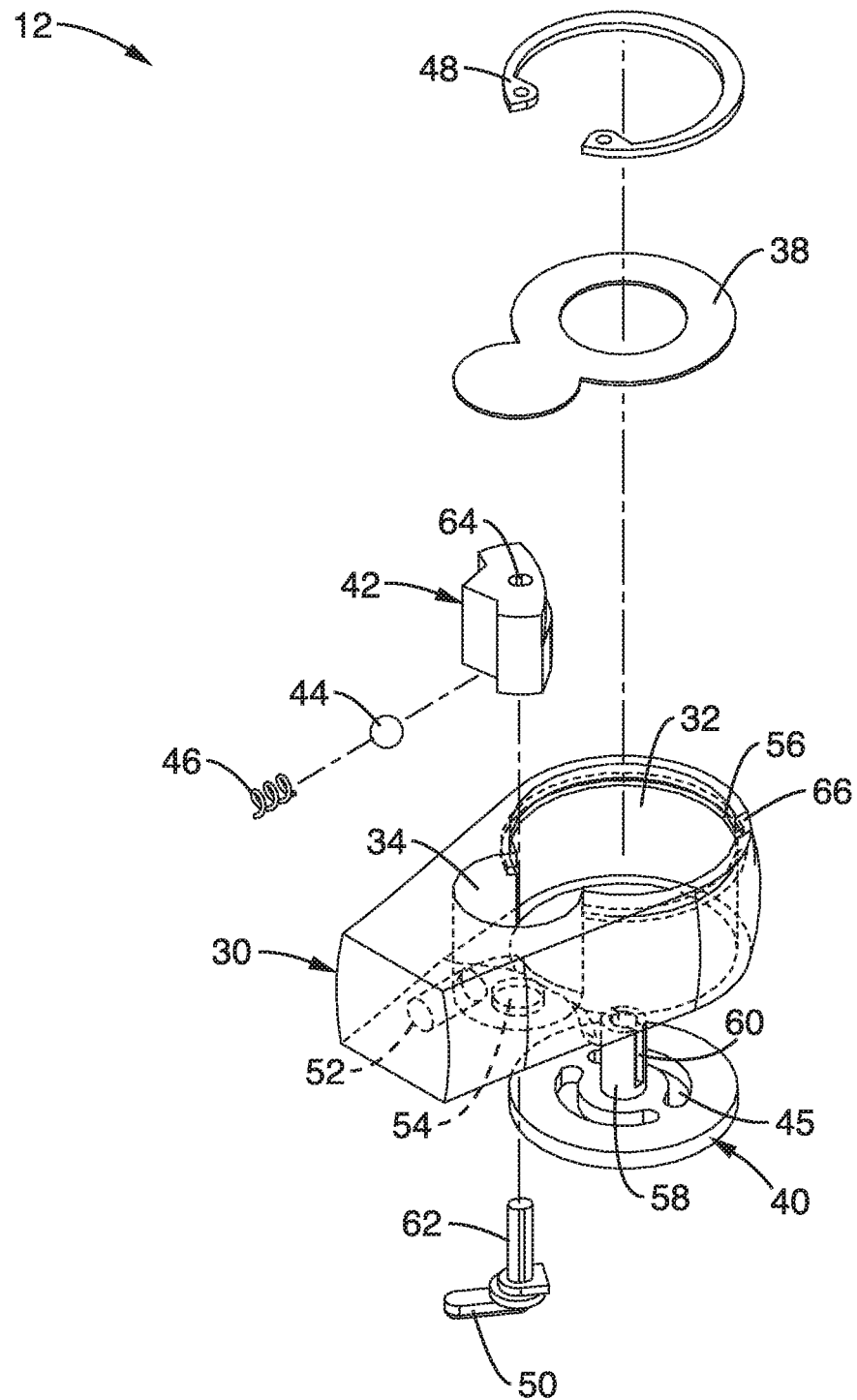
FIG. 4 shows an exploded perspective view of the ratchet mechanism of FIG. 3 without spool subassembly.

FIG. 3 through FIG. 6 show various views of the ratchet mechanism assembly 12 and components therein. FIG. 3 shows a perspective view of the ratchet mechanism 12 without the spool subassembly 70. FIG. 4 shows an exploded perspective view of the ratchet mechanism 12 of without the spool subassembly 70.

Figure 5:
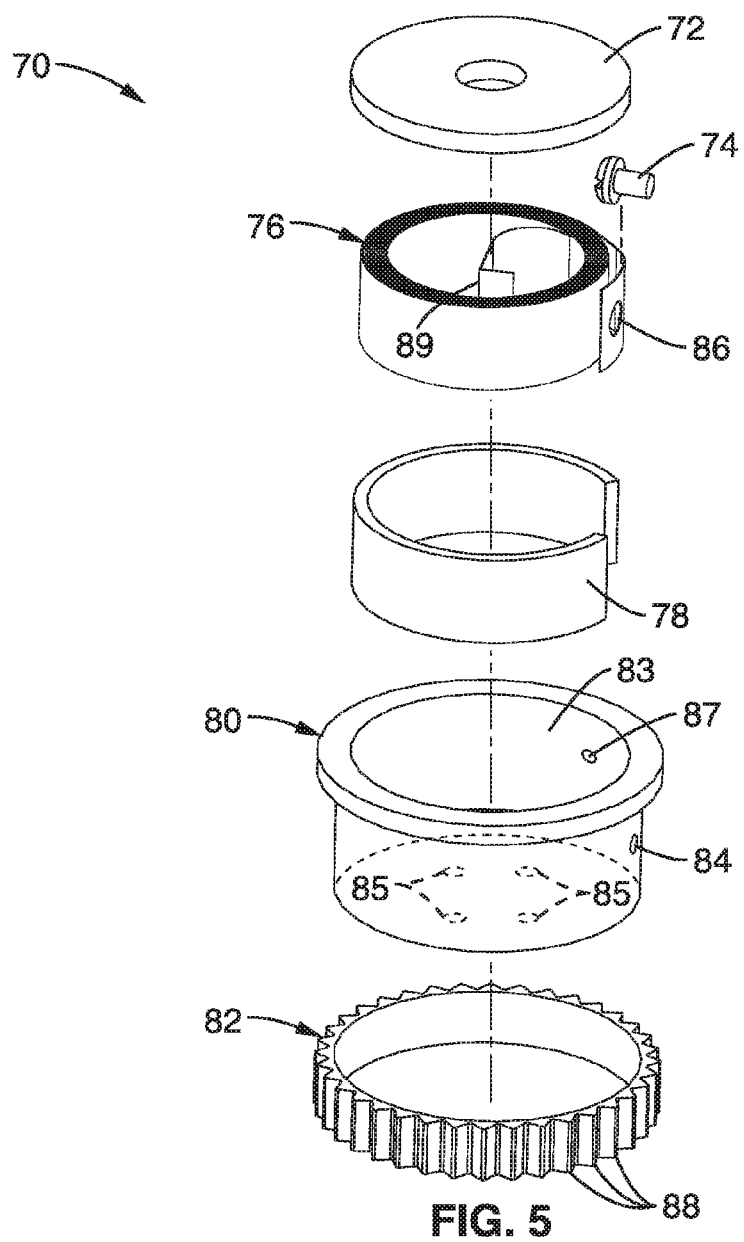
FIG. 5 shows an exploded perspective view of the spool assembly.
Figure 6:
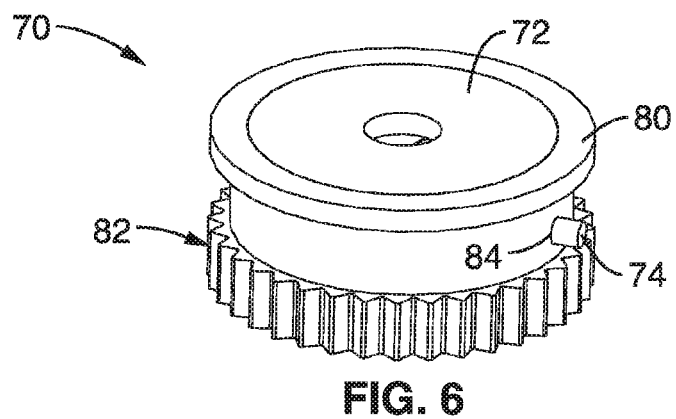
FIG. 6 shows an assembled perspective view of the spool assembly.

FIG. 5 shows an exploded perspective view of the spool subassembly 70 used in the ratchet assembly 12. FIG. 6 shows an assembled perspective view of the spool assembly 70.

The ratchet mechanism 12 primarily functions as a tendon retract and locking mechanism. The ratchet mechanism 12 comprises a housing 30 comprising a central recess or cavity 32 for housing the spool subassembly 70 (FIG. 5 and FIG. 6) and wound cable 18 upon flexion of the user's fingers. The cable 18 is wound through the housing 30 through notch 66 in the housing 30 (FIG. 4).

The bottom end of cavity 32 is capped by a removable disc-shaped base 40 comprising a central spindle member 58 extending from the base 40. The base 40 comprises a pair of semicircular slots 45 to allow for a spanner wrench or similar instrument (not shown) to interface with a pair of dowel clearance holes 85 in the spool 80 of the spool subassembly 70 (see FIG. 5), thereby allowing for a tightening torque to be applied to the cable 18.

The housing 30 further comprises a second cavity 34 for housing pawl 42. Pawl 42 comprises an ovalized through-hole 64 that interfaces with ovalized dowel 62 of the lever or toggle 50 (through bottom aperture 54 of the housing 30) such that rotation of toggle 50 affects rotation of pawl 42 for engagement and disengagement with spool assembly 70, and in particular the teeth 88 of gear 82. The pawl 42 is biased with a pawl ball 44 and pawl spring 46 that is housed in a longitudinal recess 52 to provide the ratcheting action to the system 10. Depending on the toggle position, the ball 44 and spring 46 allow for rotation of the pawl 42 in only one direction and corresponding engagement of the pawl 42 with teeth 88 of gear 82 in the opposite direction.

A shield 38 is provided to close off the cavities 32 and 34 (when spool assembly 70 and pawl 42 are positioned in place), and is secured via a snap ring 48 that is retained in circumferential groove 56 on the inner surface of the housing cavity 32.

Referring now to FIG. 5 and FIG. 6, spool subassembly 70 contains six primary components, the gear 82, spool 80, the spool cap 72, ribbon or torsion spring 76, spring attachment screw 74, and spacing ring 78.

The gear 82 comprises a ring-like structure that is attached to the bottom of the outer cylindrical wall of the spool 80 via a press fit, as shown in FIG. 6. In this position, the gear 82 is positioned to interface with the pawl 42 when the spool assembly as shown in FIG. 6 is disposed within housing cavity 32.

The torsion spring 76 is configured to be housed in cavity 83 of the spool 80 and be attached at a first end to the spool 80 via a screw 74 that fits through hole 86 and that threads into a hole 84 that is tapped perpendicular to the spool rotation. An access hole (not shown) may be provided opposite hole 94 to provide clearance for a small screwdriver. The torsion spring 76 provides the retraction force for the tendon cable 18. The second end 89 of the torsion spring 76 is attached to the housing 30 via a longitudinal slit 60 in the spindle 58 of base 40. The screw spacer 78 adds a layer the thickness of the screw 74 head height all the way around the inside of the spool 80 to allow for smoother action of the ratchet mechanism 12.

A through hole 87 is provided in spool 80 (e.g., approximately 25° away from the spring attachment hole 84) to accept one end of the cord or cable 18. The cable may be secured to the spool 80 with a knot, bead, or similar structure after installation. The gear 82, when press fit on to the spool 80, forms a bottom lip of the spool, which keeps the tendon cable 18 on the spool. A lip on the top of the spool 80 keeps the tendon cable 18 from sliding off upwards. A plurality of dowel clearance holes 85 may be located on the bottom of the spool 80 to allow for manual tightening via spanner wrench, as previously discussed. The upper end of the spool cavity 83 may comprise female threads (not shown) that mate with matching male threads (not shown) of the spool cap 72 such that the cap 72 may be threaded into the spool 80 to close off the cavity When the user closes his/her hand, the constant-torque torsion spring 76 pulls the tendon cable 18 onto the spool 80 by rotating the spool 80. If the toggle 50 rotates the pawl 42 into an engaged position, the pawl 42 will oscillate, allowing the spool 80 to rotate. When the torque from the tendon cable 18 balances with the torque from the constant-torque torsion spring 76, the system locks. The pawl 42 engagement configuration only allows the spool 80 to rotate in one direction.

To release, the toggle 50 is rotated to the disengaged position. As there are no teeth on the pawl 42 in this position, the spool 80 is free to move. The user is thus free to open his/her hand. This action pulls the tendon cable 18 out of the ratchet mechanism 12 and rotates the spool 80. The constant torque spring 76 is then tightened by the rotating spool 80.

II. Tendon Mechanism Finger Analysis

To determine the loads on the developed architecture, a single finger model was developed. This model contains the following assumptions: 1) The system is 2-dimensional, i.e., finger adduction and abduction were not included. Loads and motion lateral to the fingers was ignored. 2) Each phalange can be modeled as a rigid body, and the palm was modeled as a rigid body fixed at one end. 3) Each rigid body was connected via a pin-spring joint. 4) The stiffness of each pin-spring joint is linear (i.e., spring moment was proportional to joint angle). 5) Friction is neglected. 6) Standoffs are rigid. 7) Grip forces applied to each phalange are normal to the axis connecting the proximal and distal spring-pin joints.

Figure 7:
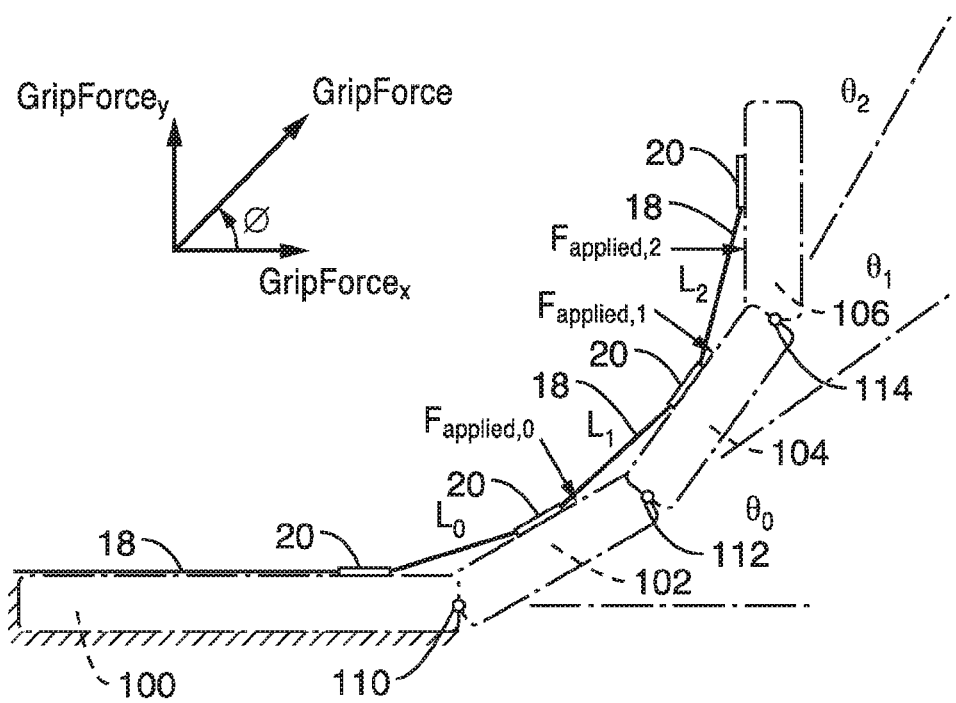
FIG. 7 is a schematic diagram of the phalange geometry and tendon drive of the present description.

FIG. 7 shows a schematic diagram depicting the proposed model with 3 phalange rigid bodies 102 (proximal phalange i=0), 104 (medial phalange i=1), and 106 (distal phalange i=2), and the fixed palm rigid body 100. MCP joint 110 (joint j=0) connects palm 100 and proximal phalange 102. PIP joint 112 (joint j=1) connects proximal phalange 102 and medial phalange 104. DIP joint 114 (joint j=2) connects medial phalange 104 and distal phalange 106. The cord or cable 18 was routed through a standoff or guide 20 located on each rigid body, as shown in FIG. 7.

Inputs to the model were as follows:

Input-1: Maximum and minimum angles for each spring-pin joint based on anthropomorphic limitations of the human finger: 0° to 90°. The model swept through all possible joint angles (with 1° of resolution) between the defined min and max angles. 90° of rotation for each joint requires $90^3=729{,}000$ individual model solutions for each set of hand geometry and cord tension.

Figure 8:
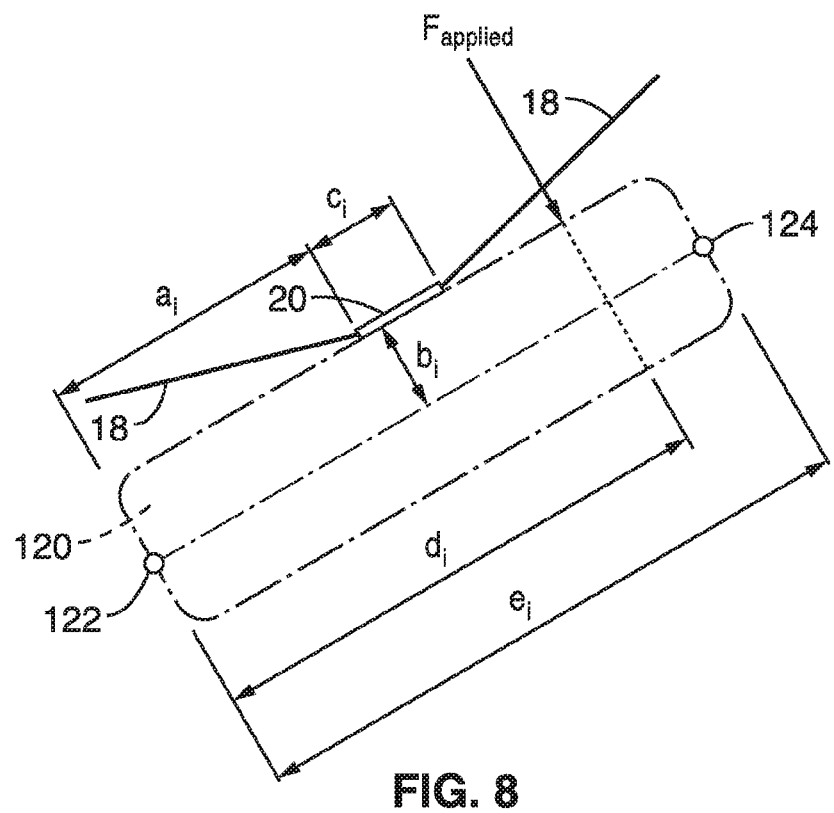
FIG. 8 is a schematic individual phalange geometry diagram with respect to a standoff of the tendon drive of the present description.

Input-2: Phalange geometry, as defined in the individual phalange geometry diagram of FIG. 8, where a is the distance between the j'th spring-pin joint 122 and the phalange guide 20, b is the distance from spring-pin connection axis and guide 20, c is the guide 20 length, d is the distance from j'th spring-pin joint 122 to the location of the external grip force, and e is the distance between j'th spring pin joint 122 and j+1'th spring-pin joint 124.

Input-3: Spring-pin stiffness was assumed linear. Details for calculating the stiffness of each spring-pin are provided below.

Input-4: Cord tension.

The model returns the following outputs:

Output-1: Three external grip forces corresponding to the grip force applied to each phalange for a static solution and the total exposed cable 18 length. Exposed length 18 is defined as the minimum distance between two adjacent guides 20. If all grip forces are positive, the solution was deemed stable. A negative grip force is non-physical.

Output-2: Total length of exposed cable 18. The minimum distance between two adjacent guides 20 was calculated, and repeated for each joint (i.e., 3 minimum distances are calculated). These distances are summed to determine the total length of exposed cable 18. This value was a function of phalange geometry and joint angles.

As no Extravehicular Mobility Unit (EMU) glove was available for testing, an analog was fabricated to simulate the semi-rigid and stiff nature of an EMU glove. The analog was fabricated from a batting glove, which was stiffened with 1 mm polystyrene in each finger.

Hand geometry varies between subjects; therefore, a single subject was selected to be measured for hand geometry and later test data. Hand geometry was taken using a middle finger. The geometry used the standard described in Input-2, and depicted in FIG. 8. Palm measurements are as follows: $a_{palm}$ is the distance between the MCP joint 110 and the distal side of the palm guide 20. When comparing to FIG. 8, $a_{palm}=e-a-c$; $b_{palm}=$vertical offset (similar to 'b' measurements in Input-2).

Figure 9:
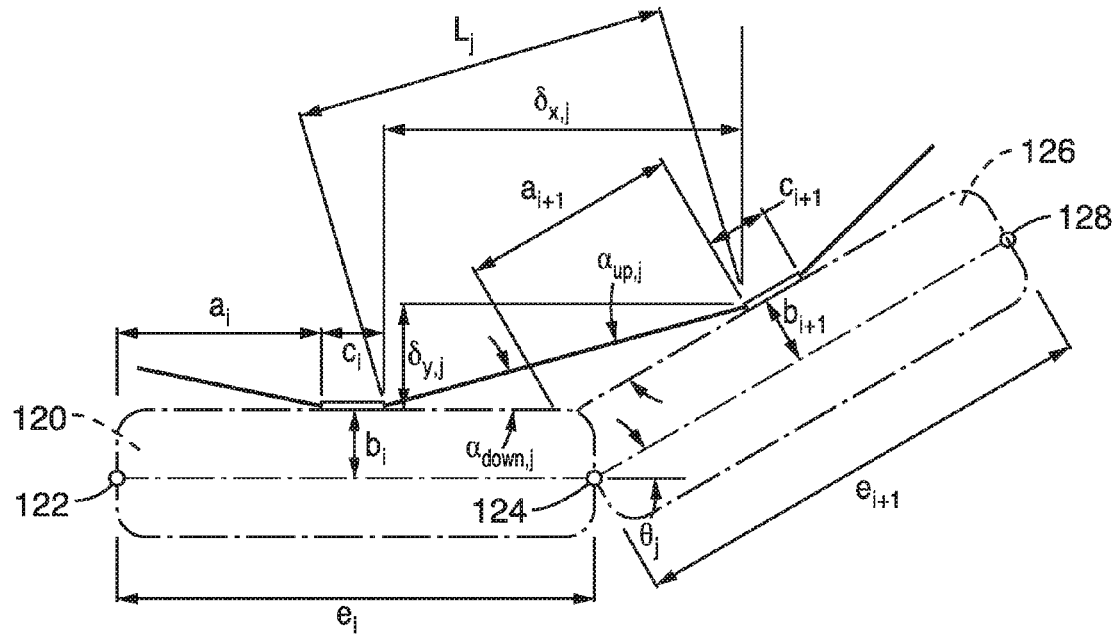
FIG. 9 is a schematic diagram illustrating the joint angles and retract length for an indexed joint and adjacent phalanges with respect to the tendon drive of the present description.

For subsequent calculations, the angles made by the cable 18 and phalange were required. A diagram showing joint j and adjacent phalanges i and i+1 is given in FIG. 9. The cable 18 angles are given as $\alpha_{up,j}$ and $\alpha_{down,j}$. The relevant geometry from the phalange geometry definition (FIG. 8) is copied in FIG. 9.

The distance terms $\delta_{x,j}$ and $\delta_{y,j}$ are calculated parameters based on the geometry of the adjacent phalanges, and the formulas are given in Eq. 1 and Eq. 2 respectively:

$$\delta_{x,j}=e_i-c_i-a_i+a_{i+1}\cos(\theta_j)-b_{i+1}\sin(\theta_j). \quad \text{Eq. 1}$$

$$\theta_{y,j}=-b_i+a_{i+1}\sin(\theta_j)+b_{i+1}\cos(\theta_j). \quad \text{Eq. 2}$$

Trigonometry was used to calculate the down cable angle $\alpha_{down,j}$ via Eq. 3:

$$\alpha_{down,j}=\tan^{-1}(\delta_{y,j}/\delta_{x,j}). \quad \text{Eq. 3}$$

The value of $\alpha_{up,j}$ was calculated as the difference between joint angle $\theta_j$ and $\alpha_{down,j}$:

$$\alpha_{up,j}=\theta_j-\alpha_{down,j}. \quad \text{Eq. 4}$$

The length of cable 18 between the guides 20 of adjacent phalanges i and i+1 is $L_j$ and was calculated in Eq. 5. This length was used to compare an open hand configuration (MCP=PIP=DIP=0°) to a closed configuration (MCP=PIP=DIP≈0°):

$$L_j=\sqrt{\delta_{x,j}^2+\delta_{y,j}^2}. \quad \text{Eq. 5}$$

To illustrate the execution of Eq. 1 through Eq. 5, the DIP joint 114 was evaluated for $\theta_2$=DIP Angle=20°. Geometry for the adjacent phalanges (distal and medial) was used as measured. The results and intermediate calculations are given in Eq. 6 through Eq. 10:

$$\delta_{x,j=2,\theta=20°} = \quad \text{Eq. 6}$$
$$e_{medial} - c_{medial} - a_{medial} + a_{distal}\cos(\theta_2) - b_{distal}\sin(\theta_2) =$$
$$11.31 \text{ mm.}$$

$$\delta_{y,j=2,\theta=20°} = -b_{medial} + a_{distal}\sin(\theta_2) + b_{distal}\cos(\theta_2) = -0.12 \text{ mm.} \quad \text{Eq. 7}$$

$$\alpha_{down,j=2,\theta=20°} = \tan^{-1}\left(\frac{\delta_{x,j=2,\theta=20°}}{\delta_{x,j=2,\theta=20°}}\right) = -0.62°. \quad \text{Eq. 8}$$

$$\alpha_{up,j=2,\theta=20°} = \theta_j - \alpha_{down,j} = 20.6°. \quad \text{Eq. 9}$$

A negative $\delta_{y,j=2,\theta=20°}$ and $\alpha_{down,j=2,\theta=20°}$ implies the cord is at a negative angle relative to the spring-pin connection axis:

$$L_{j=2,\theta=20°}=\sqrt{\delta_{x,j=2,\theta=20°}^2+\delta_{y,j=2,\theta=20°}^2}=11.31 \text{ mm.} \quad \text{Eq. 10}$$

The cable length $L_0$ at the $\theta_0$=DIP Angle=20° was compared to the cable length when $\theta_0$=DIP Angle=0°. (i.e., $L_{0,\theta=0}$). The difference between these two values is the cable length retracted $\Delta L_0$, and was calculated in Eq. 11:

$$\Delta L_{j=2,\ \theta=20°}=L_{j=2,\ \theta=0}-L_{j=2,\ \theta=20°}=3.98 \text{ mm} \quad \text{Eq. 11}$$

A change in cord length across a joint on the order of 4 mm is reasonable, and 3.98 mm was confirmed with Solidworks.

A successful under actuated hand mechanism should ideally have stiffness at each joint. Space suit gloves have inherent stiffness due to pressurization and fabric layers. To model the glove, the stiffness of the glove joints should be determined.

To develop the finger model, experimental data was collected for the batting glove analog. The test procedure to measure stiffness was performed according to the following steps: 1) A cord 1 m long was routed between the adjacent guides to the joint to be measured. The distal end of the cord was tied to the distal guide. 2) A known weight was attached to the proximal end of the cord. 3) The test subject donned the glove. 4) The test subject held his hand and forearm vertical, with elbow resting on a table. 5) The weight attached in step 2 was suspended below the table. 6) The additional weight caused the distal tested digit to rotate until the spring joint moment balanced the applied weight. The subject was instructed not to resist or assist the movement. 7) The angle of the tested joint was measured with a protractor. 8) Steps 2 through 7 were repeated for additional weights and joints.

From the angle measured step 7 of the above stiffness procedure, the spring-pin stiffness can be calculated. This was done by balancing moments of the distal phalange rigid body about the joint being analyzed. The moment generated by the cord terminating at the distal guide must be balanced by the spring-pin joint.

Figure 10:
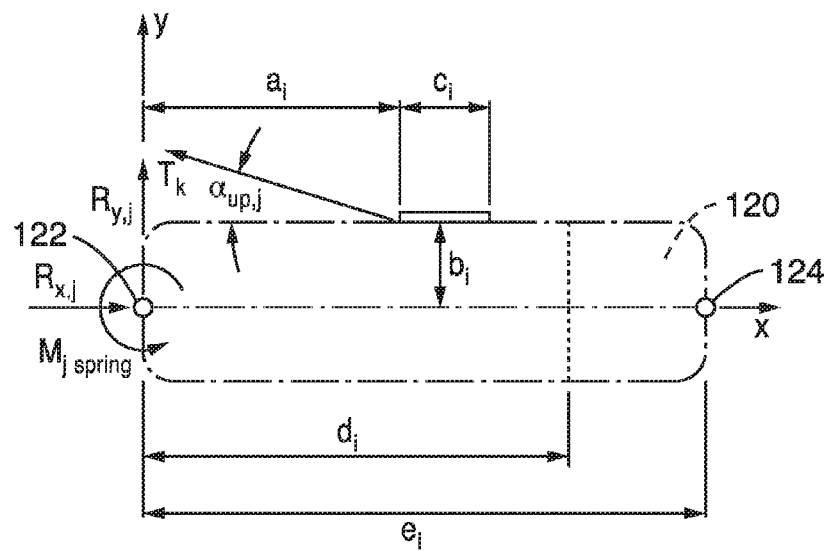
FIG. 10 shows a joint stiffness free body diagram with respect to the tendon drive of the present description.

Eq. 12 describes the relationship between cord tension and spring moment based on the free body diagram in FIG. 10. Note that the cord angle $\alpha_{up,j}$ must be determined before the moment calculation. The weight applied to the system is labeled $T_k$:

$$\Sigma M_{joint,j} = 0 = -M_{j,spring} + a_i T_k \sin(\alpha_{up,j}) + b_i T_k \cos(\alpha_{up,j}) \qquad \text{Eq. 12}$$

Solving Eq. 12 for $M_{j,spring}$ returns Eq. 13:

$$M_{j,spring} = T_k(a_i \sin(\alpha_{up,j}) + b_i \cos(\alpha_{up,j})). \qquad \text{Eq. 13}$$

Three loads were applied to three joints (totaling 9 configurations), and the angle of the joint was measured as described in step 7 of the stiffness procedure. An additional configuration of 0 load and 0 angle was included for each joint as there should be no moment when the glove is open in its neutral position. The forces applied, angles measured, and resulting moments were calculated via Eq. 13. Eq. 14 provides a sample moment balance calculation for the j=2 joint when 12 N of tension was applied to the cord. From Eq. 9, the angle between cord and spring-pin axis is 0.155 rad=8.88°. The values of $a_i$ and $b_i$ are geometric parameters for the proximal phalange acquired by measurement. The value of $\alpha_{up,j}$ is calculated from Eq. 4.

$$M_{j,spring} = 143 \text{N mm}. \qquad \text{Eq. 14}$$

The spring-pin moment was calculated as a function of measured joint angle $\theta_j$ for the three joint angles. A linear fit was applied to each data set, and the slope of the fit line is the stiffness of the spring $k_j$ via Eq. 15:

$$M_{j,spring} = k_j(\theta_j). \qquad \text{Eq. 15}$$

Therefore, the slope linear fit least squares (linear stiffness was assumed) is the stiffness of the joint. The spring-pin analysis returned the stiffness $k_j$ for each joint j of the batting glove analog.

As each phalange comprises of similar geometry, a series of equations was developed which can be applied to each phalange to determine the required external grip force as identified in Output-1. Each phalange was modeled as a rigid body in static equilibrium; the sum of forces and moments must equal zero for each phalange. Forces are split into a local x and y coordinate to simplify the equations. Therefore, there will be 9 equations for static equilibrium in total (3 rigid bodies to solve, 3 static equations each). The forces on the palm are not required as the palm is modeled as a fixed rigid body. The variables are defined as follows: $T_k$ is the tendon tension, $M_j$ is the moment due to spring-pin stiffness and joint angle j:

$$M_j = k_j \theta_j. \qquad \text{Eq. 16}$$

$M_{j+1}$ is the moment due to spring-pin stiffness and joint angle j+1. Note $M_{j+1}$ is defined positive in the opposite direction as $M_j$ to account for the inversion across joints:

$$M_{j+1} = k_{j+1} \theta_{j+1}. \qquad \text{Eq. 17}$$

$R_{x,j+1}$ is the reaction force in the local x direction, calculated from the i+1 phalange rigid body. Note that $R_{x,j+1}$ must be converted to the local reference coordinate system and orientation reversed due to the spring-pin joint, which was performed with Eq. 18:

$$R_{x,j+1} = -R_{x,j+1,\,local} \cos(\theta_j) + R_{y,j+1,\,local} \sin(\theta_j). \qquad \text{Eq. 18}$$

$R_{y,j+1}$ is the reaction force in the local x direction rigid body, calculated from the i+1 phalange. Note that $R_{y,j+1}$ needs to be converted to the local reference coordinate system and orientation reversed due to the spring-pin joint, which was performed with Eq. 19:

$$R_{x,j+1} = -R_{x,j-1,\,local} \sin(\theta_j) + R_{y,j+1,\,local} \cos(\theta_j). \qquad \text{Eq. 19}$$

$\alpha_{up,j}$ is the angle between the cord and spring-pin connection axis of joint j, based on Eq. 3. $\alpha_{down,j+1}$ is the angle between cord and spring-pin connection axis passing over joint j+1, based on Eq. 4. $F_{applied,i}$ is the normal grip force imparted from the gripped object to the phalange, calculated with Eq. 23. $R_{x,j}$ is the reaction force in the local x direction, calculated in equation Eq. 24. $R_{y,j}$ is the reaction force in the local y direction, calculated in equation Eq. 25.

As each body is in static equilibrium, the sum of moments and forces must be zero. This was enforced in Eq. 20 through Eq. 22:

$$\Sigma M_{j,thspring-pin\,joint} = 0 = M_j - M_{j+1}, T_k b_i \cos(\alpha_{up,j}) - T_k b_i \cos(\alpha_{down,j+1}) + T_k a_i \sin(\alpha_{up,j}) + T_k(a_i + c_i) \sin(\alpha_{down,j+1}) - F_{applied,i} d_i + R_{y,j+1} e_i. \qquad \text{Eq. 20}$$

$$\Sigma F_x = 0 = R_{x,j} + R_{x,j+1} + T_k \cos(\alpha_{up,j}) + T_k \cos(\alpha_{down,j-1}) \qquad \text{Eq. 21}$$

$$\Sigma F_y = 0 = R_{y,j} + R_{y,j+1} + T_k \sin(\alpha_{up,j}) + T_k \sin(\alpha_{down,j+1}) - F_{applied,i}. \qquad \text{Eq. 22}$$

Eq. 20 and Eq. 21 were solved for the unknowns $F_{applied,i}$, $R_{x,j}$, $R_{y,j}$ in Eq. 23 through Eq. 25. All other variables are inputs to these equations.

$$F_{applied,i} = [M_j - M_{j+1}, T_k b_i \cos(\alpha_{up,j}) - T_k b_i \cos(\alpha_{down,j+1}) + T_k a_i \sin(\alpha_{up,j}) + T_k(a_i + c_i) \sin(\alpha_{down,j+1}) - F_{applied,i} d_i + R_{y,j+1} e_i]/d_i \qquad \text{Eq. 23}$$

$$R_{x,j} = -R_{x,j+1} + T_k \cos(\alpha_{up,j}) - T_k \cos(\alpha_{down,j+1}) \qquad \text{Eq. 24}$$

$$R_{y,j} = -R_{y,j+1} - T_k \sin(\alpha_{up,j}) - T_k \sin(\alpha_{down,j+1}) + F_{applied,i} \qquad \text{Eq. 25}$$

For Eq. 23 through Eq. 25, and Eq. 16 through Eq. 19, the previously calculated stiffness $k_j$ and acquired geometry measurements were used to solve for the three unknowns $F_{applied,i}$, $R_{x,j}$, $R_{y,j}$, for a single phalange rigid body.

To solve for the whole finger, Eq. 23 through Eq. 25, and Eq. 16 through Eq. 19 were first applied to the distal (i=2 phalange) with $R_{x,j}=3=0$, $R_{y,j}=3=0$, and $M_j=3=0$ for a given angle combination. The values for $F_{applied,2}$, $R_{x,j}=2$ and $R_{y,j}=2$ were recorded.

Reactions forces $R_{x,j}=2$ and $R_{y,j}=2$ from the distal phalange were converted to the local medial coordinate system via Eq. 18 and Eq. 19. Eq. 23 through Eq. 25 were applied again to solve for the PIP joint j=1 values $R_{x,j}=1$ and $R_{y,j}=1$, in addition to $F_{applied,i}$. Solving the proximal phalange equations used the same procedure as used in solving the medial phalange equations. Therefore, 9 force/moment balance equations were used to solve the static system.

Solving Eq. 23 through Eq. 25 for each phalange (i.e., 3 sets of 3 equations) results in an array of solutions. This array is defined by the prescribed tension in the cord 18 and list of joint angle combinations. Acceptable solutions are solutions where $F_{applied,i} \geq 0$ for all i.

The length of cord between each joint guide 20 was calculated using Eq. 5, and the sum of the cord length is given in Eq. 26. The cable length $L_{total}$ is a function of geometry:

$$L_{total} = \Sigma_{j=0}^{2} L_{i\theta j} = L_{0,\theta 0} + L_{1,\theta 1} + L_{2,\theta 2}. \quad \text{Eq. 26}$$

The retracted length is found by subtracting the sum of cord length when all joints are at 0° from the configuration to be analyzed, and is shown in Eq. 27:

$$\Delta L_{total} = L_{total, \theta o, 1, 2} - L_{total, \theta o, 1, 2 \neq 0}. \quad \text{Eq. 27}$$

The grip force for a given hand configuration ($\theta_0$, 74$_1$, $\theta_2$) and tension $T_k$ is calculated as a vector sum of the individual $F_{applied}$ terms for each phalange. The diagram showing the summed force and individual $F_{applied,i}$ terms is given in FIG. 7. The result of summed $F_{applied}$ in x and y for static equilibrium is given in Eq. 28 and Eq. 29 where GripForce$_x$ and GripForce$_y$ are the forces exerted on the gripped item. The magnitude and direction of the grip force GripForce was calculated with Eq. 30 and Eq. 31, respectively, where $\phi$ is measured from the x axis:

$$GripForce_x = \\ -F_{applied,i=0} \cos\left(\frac{3\pi}{2} + \theta_0\right) - F_{applied,i=1} \cos\left(\frac{3\pi}{2} + \theta_0 + \theta_1\right) = \\ F_{applied,i=2} \cos\left(\frac{3\pi}{2} + \theta_0 + \theta_1 + \theta_2\right). \quad \text{Eq. 28}$$

$$GripForce_y = \\ -F_{applied,i=0} \sin\left(\frac{3\pi}{2} + \theta_0\right) - F_{applied,i=1} \sin\left(\frac{3\pi}{2} + \theta_0 + \theta_1\right) = \\ F_{applied,i=2} \sin\left(\frac{3\pi}{2} + \theta_0 + \theta_1 + \theta_2\right). \quad \text{Eq. 29}$$

$$GripForce = \sqrt{GripForce_x^2 + GripForce_y^2}. \quad \text{Eq. 30}$$

$$\Phi = \tan^{-1} \frac{GripForce_y}{GripForce_x}. \quad \text{Eq. 31}$$

III. Validation and Testing

To validate the finger model generated, data was taken with the batting glove analog. Known weight was attached to the cord, and the weight was suspended under the batting glove analog. The test subject gripped a hydraulic hand dynamometer (Jamar with grip-bar in the 2nd position indexed from the palm-bar) with his middle finger, and instructed to keep his/her arm and hand vertical while keeping the weight off the floor. The following data was recorded for each test: Weight Applied ($T_k$), MCP angle ($\theta_0$), PIP angle ($\theta_1$), and DIP angle ($\theta_2$).

Figure 11:
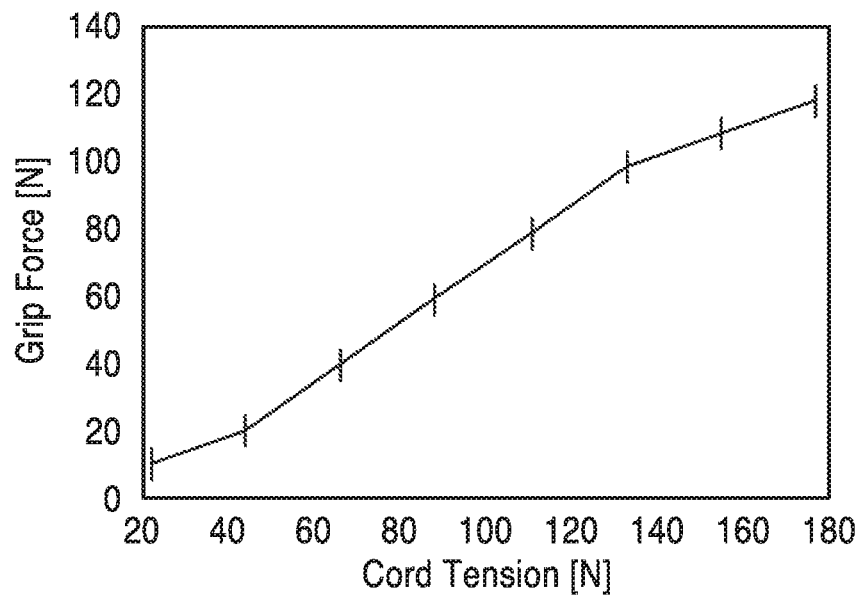
FIG. 11 shows a plot of measured grip force for validation of the finger model.
Figure 12:
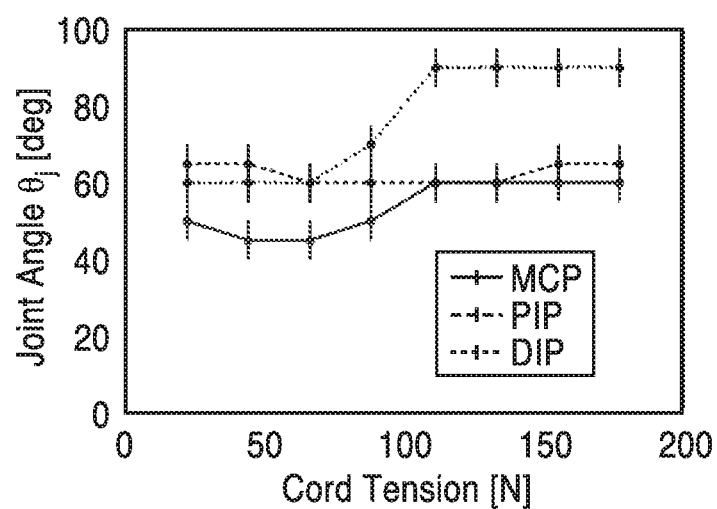
FIG. 12 shows a plot of measured joint angles for validation of the finger model.

Joint angles were measured using a finger protractor on the back of the fingers. Seven weights were tested, and FIG. 11 shows a plot of measured grip force ($T_k$ vs. GripForce). FIG. 12 shows a plot of measured joint angles ($\theta_0$, $\theta_1$, $\theta_2$) vs. cord tension $T_k$. Note the error bars in FIG. 11 and FIG. 12 represent the measurement error of the dynamometer only.

Figure 13:
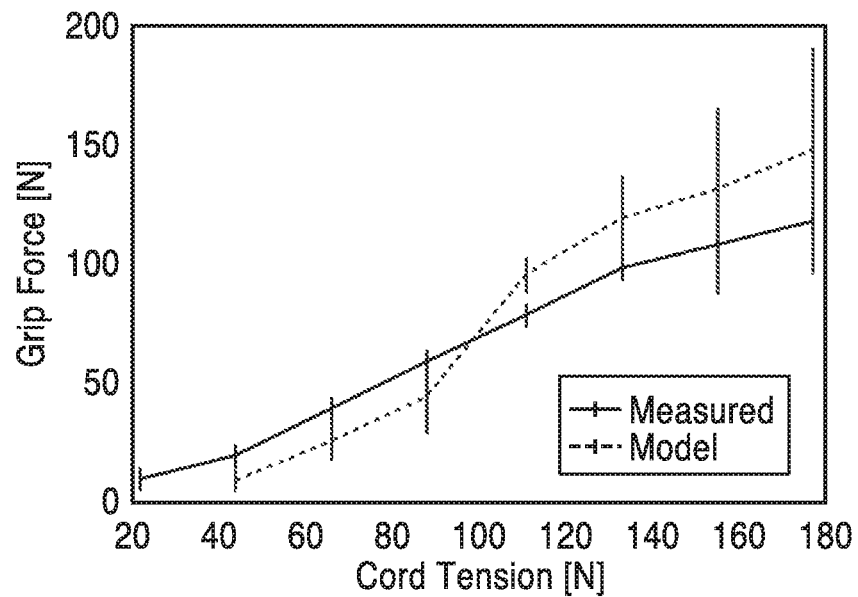
FIG. 13 shows a plot of measured grip force compared to predicted grip force.

FIG. 13 shows a plot of measured grip force compared to predicted grip force. The model and measured data have similar trends, and the solutions are on the same order. The model results predicted lower grip force than observed in testing, and the model grip forces are larger than measured grip forces above 90 N. The range of predicted grip force from the model increases with increasing cord tension. Disparity between the model and measured grip force might be attributed to the following factors: 1) out-of-plane forces: as this model is 2D in nature, any interactions out of plane are not captured by the model; 2) phalange dimension $d_i$: the geometric point where $F_{applied, i}$ is acting on the model, defined as $d_i$ in FIG. 10. Dimension $d_i$ will vary depending on the object gripped and cord tension; 3) grip force angle $\phi$: only grip force magnitude was analyzed, and it was assumed to be in line with the predicted grip force angles from Eq. 31. The grip force angle $\phi$ varied for each solution, but remained between −130° and −160° relative to the palm rigid body.

A sensitivity study of geometry was also completed to analyze the impact of geometric input to the model, and the geometry differences' impact on grip force. The geometric study was completed independent of angle ranges used in FIG. 13, as the solution space would be large and difficult to analyze. Therefore, the measured joint angles for each tension were used to determine the average grip force for a given cord tension.

Figure 14:
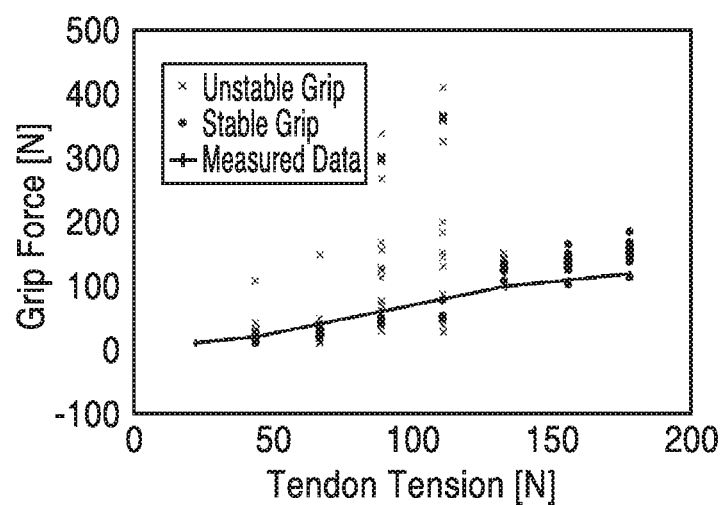
FIG. 14 shows a plot of grip force sensitivity.

Each geometric parameter for the phalanges ($a_i$, $b_i$, $c_i$, $d_i$, $e_i$) and the palm geometric parameters ($a_{palm}$ and $b_{palm}$) were varied by ±10% independently (see FIG. 10 for definition of geometric parameters). Variation of geometric parameters returned varying grip forces. However, multiple geometric changes returned unstable grip configurations. The grip force predicted by varying each geometric parameter ±10% is plotted as a function of cord tension in FIG. 14. The model did not predict any stable configurations at 22 N.

To analyze the relative error from the model, the results were compared to unmodified results for each tension. The comparison was performed by calculating absolute relative error with Eq. 32 for the glove phalange configuration averaged from stable grips found in FIG. 13. The "truth" or "unmodified" values were determined by averaging stable solutions for each tension.

Analyzing the data results in the following findings:

1. If the assumption is made that the model is linear, a 10% change in input values will result in a 10% change of output values. Many values when varied do not change by more than 10% for stable conditions. However, when changing the value for $a_1$ (distance from joint 0 to the proximal guide along the phalange axis), significant grip strength error is recorded at 18.79%. Therefore, $a_1$ is a very sensitive geometric property.

2. It was shown that variation of geometry has a small impact on the number of model-predicted unstable grip configurations. Only $b_1$ and $c_1$ were shown to have impact on the number of stable hand configuration s, but not by significant margins (±2 unstable configurations vs. the average).

3. The percent error as a function of tension was over 30% on a case-by-case basis for $T_k$=111N (see FIG. 5.14). The geometric values with more than 30% error at $T_k$=111N are $b_1$ and $c_1$. While this shows high sensitivity for a large grip force, it also shows $b_1$ and $c_1$ are not sensitive in regards to grip configuration stability.

4. The number of errors remains relatively constant except for the notable exception of 67 N. There are only 8 instances where variation of a parameter resulted in an unstable configuration. It is hypothesized that the low count of unstable configurations occurred because the angle configuration was in the middle of a stable region.

In conclusion, the sensitivity study has shown that $a_1$, $b_1$, $c_1$, and $b_2$ are critical geometric dimensions. It was unexpected that $d_i$ was not a critical dimension, as this value determines $F_{applied,i}$ for each phalange. However, in overall sensitivity the joint angles $\theta_j$ were shown to be more sensitive than geometry.

While the embodiments above are primarily detailed for use with a pressured glove for EVA applications, it is appreciated that the passive mechanical exoskeleton system 10 may be configured for a variety of uses. For example, many applications require laborers to hold onto tools or other equipment for extended duration. A modified version of system 10 may be adapted to a work glove, or similar garment. This system would allow the laborer to use the tool for an extended period without hand fatigue.

Furthermore, many jobs require a tether for safety concerns. In some implementations, the system 10 can be adapted to serve as a tether to hold a laborer and provide fall protection.

Many sports require extended grip strength or bindings. While the description above is detailed with respect to a glove to be worn over the hand and fingers, it is appreciated that the technology may be directed to any appendage or body member (e.g., feet, legs, arms, spine, etc.), particularly where the body member is free to move in extension/flexion, etc. For example, the passive mechanical exoskeleton system 10 may be applied to binding technology for snow board boots (and similar shoe wear), and to braces or other forms of orthopedic devices.

From the description herein, it will be appreciated that that the present disclosure encompasses multiple embodiments which include, but are not limited to, the following:

1. A system for assisting hand operation, the system comprising: (a) a tendon drive mechanism, comprising: (i) one or more cables having a distal end configured to be coupled to a distal location on one or more fingers of a hand of a user; (ii) one or more guides configured to couple to the one or more fingers at one or more palmar locations corresponding to phalanges of the one or more fingers; (iii) the one or more guides configured to guide translation of the one or more cables upon flexion or extension of the one or more fingers; and (b) a ratchet mechanism coupled to the tendon drive mechanism, comprising: (i) a spool configured to receive a proximal end of at least one of the one or more cables, the spool being passively biased and keep taught the receive at least one of the one or more cables upon flexion of the one or more fingers and selectively allow extension of the one or more fingers; and (ii) a locking mechanism coupled to the spool, the locking mechanism comprising a non-engaged orientation allowing flexion and extension of the one or more fingers and an engaged orientation allowing flexion while restraining extension of the one or more fingers such that the tendon drive mechanism and ratchet mechanism are operable to retain the hand in a selected grasping position.

2. The system of any of the preceding embodiments, wherein the tendon drive mechanism and ratchet mechanism are integrated with or attached to a glove configured to be worn over the hand of the user.

3. The system of any of the preceding embodiments, wherein the one or more guides comprise tubes attached to or integrated with the glove, the guides configured to slideably retain one of the one or more cables at a plurality of locations corresponding to separate locations on distinct phalanges of an individual finger such that flexion of the finger shortens a distance between the plurality of guides proportional to a shortening of a length of the cable passing through the plurality of guides.

4. The system of any of the preceding embodiments, wherein the tubes are located at locations corresponding to a palmar surface of the hand, along with a proximal phalange location, medial phalange location and distal phalange location of an individual finger.

5. The system of any of the preceding embodiments: wherein the ratchet mechanism is positioned on the glove at a dorsal location with respect to the hand when worn on the user; and wherein the tendon drive mechanism further comprises a sleeve configured to house the one or more cables from a palmer location and extend to the ratchet mechanism around the hand to the dorsal location.

6. The system of any of the preceding embodiments: wherein the ratchet mechanism comprises a pawl configured to interface with a gear fixedly coupled to the spool; wherein when the ratchet mechanism is in the non-engaged orientation, the pawl is not engaged with the gear to allow two-way reciprocation of the one or more cables within the spool to allow flexion and extension of the one or more fingers; and wherein when the ratchet mechanism is in the engaged orientation, the pawl is engaged with the gear to allow only one-way reciprocation of the one or more cables into the spool, thus allowing flexion while restraining extension of the one or more fingers.

7. The system of any of the preceding embodiments, further comprising: a toggle coupled to the pawl; the toggle allowing for manual reciprocation of the pawl between the non-engaged orientation and engaged orientation.

8. The system of any of the preceding embodiments, wherein the spool is biased with a constant torque torsion spring to provide a tensile force on the one or more cables such that the cables automatically wind into the spool upon flexion of the one or more fingers.

9. A glove assembly configured for assisting hand operation, the glove comprising:(a) a glove configured to be worn around the hand of a user, the glove comprising a tendon drive mechanism and a ratchet mechanism; (b) the tendon drive mechanism comprising: (i) one or more cables having a distal end configured to be attached to a distal location on the glove corresponding to one or more fingers of the user's hand; (ii) one or more guides attached to the glove at one or more palmar locations corresponding to phalanges of the one or more fingers; (iii) the one or more guides configured to guide translation of the one or more cables upon flexion or extension of the one or more fingers; and (b) a ratchet mechanism attached to the glove at a dorsal location of the glove and coupled to the tendon drive mechanism, the ratchet mechanism comprising: (i) a spool configured to receive a proximal end of at least one of the one or more cables, the spool being passively biased and keep taught the receive at least one of the one or more cables upon flexion of the one or more fingers and selectively allow extension of the one or more fingers; and (ii) a locking mechanism coupled to the spool, the locking mechanism comprising a non-engaged orientation allowing flexion and extension of the one or more fingers and an engaged orientation allowing flexion while restraining extension of the one or more fingers such that the tendon drive mechanism and ratchet mechanism are operable to retain the hand in a selected grasping position.

10. The glove assembly of any of the preceding embodiments, wherein the one or more guides comprise tubes attached to or integrated with the glove, the tubes configured to slideably retain one of the one or more cables at a plurality of locations corresponding to separate locations on distinct phalanges of an individual finger such that flexion of the finger shortens a distance between the plurality of guides proportional to a shortening of a length of the cable passing through the plurality of tubes.

11. The glove assembly of any of the preceding embodiments, wherein the tubes are attached to the glove at locations corresponding to a palmar surface of the hand, along with a proximal phalange location, medial phalange location and distal phalange location of an individual finger.

12. The glove assembly of any of the preceding embodiments, wherein the tendon drive mechanism further comprises a sleeve configured to house the one or more cables from a palmer location and extend to the ratchet mechanism around the hand to the dorsal location.

13. The glove assembly of any of the preceding embodiments: wherein the ratchet mechanism comprises a pawl configured to interface with a gear fixedly coupled to the spool; wherein when the ratchet mechanism is in the non-engaged orientation, the pawl is not engaged with the gear to allow two-way reciprocation of the one or more cables within the spool to allow flexion and extension of the one or more fingers; and wherein when the ratchet mechanism is in the engaged orientation, the pawl is engaged with the gear to allow only one-way reciprocation of the one or more cables into the spool, thus allowing flexion while restraining extension of the one or more fingers.

14. The glove assembly of any of the preceding embodiments, further comprising: a toggle coupled to the pawl; the toggle allowing for manual reciprocation of the pawl between the non-engaged orientation and engaged orientation.

15. The glove assembly of any of the preceding embodiments, wherein the spool is biased with a constant torque torsion spring to provide a tensile force on the one or more cables such that the cables automatically wind into the spool upon flexion of the one or more fingers.

16. The glove assembly of any of the preceding embodiments, wherein the glove comprises a pressurized glove.

17. The glove assembly of any of the preceding embodiments, wherein the glove comprises a tether configured to retain the user at a specified location.

18. A passive mechanical exoskeleton system comprising: (a) a tendon drive mechanism, comprising: (i) one or more cables having a distal end configured to be coupled to a distal location of an appendage of a user; (ii) one or more guides configured to couple to the appendage at one or more locations corresponding to a joint associated with the appendage; (iii) the one or more guides configured to guide translation of the one or more cables upon flexion or extension of the appendage; and (b) a ratchet mechanism coupled to the tendon drive mechanism, comprising: (i) a spool configured to receive a proximal end of at least one of the one or more cables, the spool being passively biased and keep taught the receive at least one of the one or more cables upon flexion of the appendage and selectively allow extension of the appendage; and (ii) a locking mechanism coupled to the spool, the locking mechanism comprising a non-engaged orientation allowing flexion and extension of the appendage and an engaged orientation allowing flexion while restraining extension of the appendage such that the tendon drive mechanism and ratchet mechanism are operable to retain the appendage in a selected position.

19. The system of any of the preceding embodiments, wherein the tendon drive mechanism and ratchet mechanism are integrated with or attached to a garment configured to be worn over the appendage.

20. The system of any of the preceding embodiments, wherein the one or more guides comprise tubes attached to or integrated with the garment, the guides configured to slideably retain one of the one or more cables at a plurality of locations corresponding to separate locations on distinct locations of the appendage such that flexion of the appendage shortens a distance between the plurality of guides proportional to a shortening of a length of the cable passing through the plurality of guides.

21. The system of any of the preceding embodiments: wherein the ratchet mechanism comprises a pawl configured to interface with a gear fixedly coupled to the spool; wherein when the ratchet mechanism is in the non-engaged orientation, the pawl is not engaged with the gear to allow two-way reciprocation of the one or more cables within the spool to allow flexion and extension of the appendage; and wherein when the ratchet mechanism is in the engaged orientation, the pawl is engaged with the gear to allow only one-way reciprocation of the one or more cables into the spool, thus allowing flexion while restraining extension of the appendage.

22. The system of any of the preceding embodiments, further comprising: a toggle coupled to the pawl; the toggle allowing for manual reciprocation of the pawl between the non-engaged orientation and engaged orientation.

23. The system of any of the preceding embodiments, wherein the spool is biased with a constant torque torsion spring to provide a tensile force on the one or more cables such that the cables automatically wind into the spool upon flexion of the appendage.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for assisting hand operation, the system comprising:
   (a) a tendon drive mechanism, comprising:
      (i) one or more cables having a distal end configured to be coupled to a distal location on one or more fingers of a hand of a user;
      (ii) one or more guides configured to couple to the one or more fingers at one or more palmar locations corresponding to phalanges of the one or more fingers;
      (iii) the one or more guides configured to guide translation of the one or more cables upon flexion or extension of the one or more fingers; and
   (b) a ratchet mechanism coupled to the tendon drive mechanism, comprising:
      (i) a passively biased spool configured to receive a proximal end of at least one of the one or more cables and keep taught at least one of the one or more cables upon flexion of the one or more fingers and selectively allow extension of the one or more fingers; and (ii) a locking mechanism coupled to the spool, the locking mechanism comprising a non-engaged orientation allowing flexion and extension of the one or more fingers and an engaged orientation allowing flexion while restraining extension of the one or more fingers such that the tendon drive mechanism and ratchet mechanism are operable to retain the hand in a selected grasping position.

2. The system of claim 1, wherein the tendon drive mechanism and ratchet mechanism are integrated with or attached to a glove configured to be worn over the hand of the user.

3. The system of claim 2, wherein the one or more guides comprise tubes attached to or integrated with the glove, the guides configured to slideably retain one of the one or more cables at a plurality of locations corresponding to separate locations on distinct phalanges of an individual finger such that flexion of the finger shortens a distance between the plurality of guides proportional to a shortening of a length of the cable passing through the plurality of guides.

4. The system of claim 3, wherein the tubes are located at locations corresponding to a palmar surface of the hand, along with a proximal phalange location, medial phalange location and distal phalange location of an individual finger.

5. The system of claim 2:
wherein the ratchet mechanism is positioned on the glove at a dorsal location with respect to the hand when worn on the user; and
wherein the tendon drive mechanism further comprises a sleeve configured to house the one or more cables from a palmer location and extend to the ratchet mechanism around the hand to the dorsal location.

6. The system of claim 1:
wherein the ratchet mechanism comprises a pawl configured to interface with a gear fixedly coupled to the spool;
wherein when the ratchet mechanism is in the non-engaged orientation, the pawl is not engaged with the gear to allow two-way reciprocation of the one or more cables within the spool to allow flexion and extension of the one or more fingers; and
wherein when the ratchet mechanism is in the engaged orientation, the pawl is engaged with the gear to allow only one-way reciprocation of the one or more cables into the spool, thus allowing flexion while restraining extension of the one or more fingers.

7. The system of claim 6, further comprising:
a toggle coupled to the pawl;
the toggle allowing for manual reciprocation of the pawl between the non-engaged orientation and engaged orientation.

8. The system of claim 1, wherein the spool is biased with a constant torque torsion spring to provide a tensile force on the one or more cables such that the cables automatically wind into the spool upon flexion of the one or more fingers.

9. A glove assembly configured for assisting hand operation, the glove comprising:
(a) a glove configured to be worn around the hand of a user, the glove comprising a tendon drive mechanism and a ratchet mechanism;
(b) the tendon drive mechanism comprising:
(i) one or more cables having a distal end configured to be attached to a distal location on the glove corresponding to one or more fingers of the user's hand;
(ii) one or more guides attached to the glove at one or more palmar locations corresponding to phalanges of the one or more fingers;
(iii) the one or more guides configured to guide translation of the one or more cables upon flexion or extension of the one or more fingers; and
(c) a ratchet mechanism attached to the glove at a dorsal location of the glove and coupled to the tendon drive mechanism, the ratchet mechanism comprising:
(i) a passively biased spool configured to receive a proximal end of at least one of the one or more cables and keep taught at least one of the one or more cables upon flexion of the one or more fingers and selectively allow extension of the one or more fingers; and
(ii) a locking mechanism coupled to the spool, the locking mechanism comprising a non-engaged orientation allowing flexion and extension of the one or more fingers and an engaged orientation allowing flexion while restraining extension of the one or more fingers such that the tendon drive mechanism and ratchet mechanism are operable to retain the hand in a selected grasping position.

10. The glove assembly of claim 9, wherein the one or more guides comprise tubes attached to or integrated with the glove, the tubes configured to slideably retain one of the one or more cables at a plurality of locations corresponding to separate locations on distinct phalanges of an individual finger such that flexion of the finger shortens a distance between the plurality of guides proportional to a shortening of a length of the cable passing through the plurality of tubes.

11. The glove assembly of claim 10, wherein the tubes are attached to the glove at locations corresponding to a palmar surface of the hand, along with a proximal phalange location, medial phalange location and distal phalange location of an individual finger.

12. The glove assembly of claim 9, wherein the tendon drive mechanism further comprises a sleeve configured to house the one or more cables from a palmer location and extend to the ratchet mechanism around the hand to the dorsal location.

13. The glove assembly of claim 9:
wherein the ratchet mechanism comprises a pawl configured to interface with a gear fixedly coupled to the spool;
wherein when the ratchet mechanism is in the non-engaged orientation, the pawl is not engaged with the gear to allow two-way reciprocation of the one or more cables within the spool to allow flexion and extension of the one or more fingers; and
wherein when the ratchet mechanism is in the engaged orientation, the pawl is engaged with the gear to allow only one-way reciprocation of the one or more cables into the spool, thus allowing flexion while restraining extension of the one or more fingers.

14. The glove assembly of claim 13, further comprising:
a toggle coupled to the pawl;
the toggle allowing for manual reciprocation of the pawl between the non-engaged orientation and engaged orientation.

15. The glove assembly of claim 9, wherein the spool is biased with a constant torque torsion spring to provide a tensile force on the one or more cables such that the cables automatically wind into the spool upon flexion of the one or more fingers.

16. The glove assembly of claim 9, wherein the glove comprises a pressurized glove.

17. The glove assembly of claim 9, wherein the glove comprises a tether configured to retain the user at a specified location.

18. A passive mechanical exoskeleton system comprising:
(a) a tendon drive mechanism, comprising:
 (i) one or more cables having a distal end configured to be coupled to a distal location of an appendage of a user;
 (ii) one or more guides configured to couple to the appendage at one or more locations corresponding to a joint associated with the appendage;
 (iii) the one or more guides configured to guide translation of the one or more cables upon flexion or extension of the appendage; and
(b) a ratchet mechanism coupled to the tendon drive mechanism, comprising:
 (i) a passively biased spool configured to receive a proximal end of at least one of the one or more cables and keep taught at least one of the one or more cables upon flexion of the appendage and selectively allow extension of the appendage; and
 (ii) a locking mechanism coupled to the spool, the locking mechanism comprising a non-engaged orientation allowing flexion and extension of the appendage and an engaged orientation allowing flexion while restraining extension of the appendage such that the tendon drive mechanism and ratchet mechanism are operable to retain the appendage in a selected position.

19. The system of claim 18, wherein the tendon drive mechanism and ratchet mechanism are integrated with or attached to a garment configured to be worn over the appendage.

20. The system of claim 19, wherein the one or more guides comprise tubes attached to or integrated with the garment, the guides configured to slideably retain one of the one or more cables at a plurality of locations corresponding to separate locations on distinct locations of the appendage such that flexion of the appendage shortens a distance between the plurality of guides proportional to a shortening of a length of the cable passing through the plurality of guides.

21. The system of claim 18:
 wherein the ratchet mechanism comprises a pawl configured to interface with a gear fixedly coupled to the spool;
 wherein when the ratchet mechanism is in the non-engaged orientation, the pawl is not engaged with the gear to allow two-way reciprocation of the one or more cables within the spool to allow flexion and extension of the appendage; and
 wherein when the ratchet mechanism is in the engaged orientation, the pawl is engaged with the gear to allow only one-way reciprocation of the one or more cables into the spool, thus allowing flexion while restraining extension of the appendage.

22. The system of claim 21, further comprising:
 a toggle coupled to the pawl;
 the toggle allowing for manual reciprocation of the pawl between the non-engaged orientation and engaged orientation.

23. The system of claim 18, wherein the spool is biased with a constant torque torsion spring to provide a tensile force on the one or more cables such that the cables automatically wind into the spool upon flexion of the appendage.

* * * * *